(12) United States Patent
Sajiki et al.

(10) Patent No.: US 8,293,046 B2
(45) Date of Patent: Oct. 23, 2012

(54) PROCESS FOR PRODUCTION OF POROUS BODY AND USES THEREOF

(75) Inventors: Toshinobu Sajiki, Hiroshima (JP); Satoshi Hirai, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 590 days.

(21) Appl. No.: 12/518,386

(22) PCT Filed: Mar. 24, 2008

(86) PCT No.: PCT/JP2008/055465
§ 371 (c)(1),
(2), (4) Date: Jun. 9, 2009

(87) PCT Pub. No.: WO2008/120602
PCT Pub. Date: Oct. 9, 2008

(65) Prior Publication Data
US 2009/0319016 A1 Dec. 24, 2009

(30) Foreign Application Priority Data
Mar. 30, 2007 (JP) ................................. 2007-092025

(51) Int. Cl.
*B29C 65/00* (2006.01)

(52) U.S. Cl. ........ 156/80; 156/242; 156/281; 156/308.2

(58) Field of Classification Search .................... 156/80, 156/242, 281, 308.2, 309.9; 623/23.72, 23.76; 424/423, 426
See application file for complete search history.

(56) References Cited

U.S. PATENT DOCUMENTS

| | | | | |
|---|---|---|---|---|
| 4,238,480 | A | * 12/1980 | Sawyer | 514/13.8 |
| 4,606,910 | A | * 8/1986 | Sawyer | 424/423 |
| 5,188,825 | A | * 2/1993 | Iles et al. | 424/78.1 |
| 5,514,378 | A | 5/1996 | Mikos et al. | |
| 5,607,474 | A | 3/1997 | Athaasiou et al. | |
| 5,674,286 | A | * 10/1997 | D'Alessio et al. | 424/423 |
| 5,861,034 | A | * 1/1999 | Taira et al. | 623/11.11 |
| 6,303,697 | B1 | * 10/2001 | Yuan et al. | 525/240 |
| 6,306,424 | B1 | 10/2001 | Vyakarnam et al. | |
| 6,333,029 | B1 | 12/2001 | Vyakarnam et al. | |
| 6,626,950 | B2 | 9/2003 | Brown et al. | |
| 7,824,701 | B2 | * 11/2010 | Binette et al. | 424/423 |

(Continued)

FOREIGN PATENT DOCUMENTS

JP  2-265935  10/1990

(Continued)

*Primary Examiner* — John Goff
(74) *Attorney, Agent, or Firm* — Hamre, Schumann, Mueller & Larson, P.C.

(57) ABSTRACT

A process for producing a porous body with different physical properties in desired regions is provided by pore forming treatment, not by bonding two or more materials made porous beforehand, with, for example, an adhesive. Raw materials are prepared, each of which contains a polymer and a raw material preparation solvent. At least two types of the raw materials having different compositions are prepared. Thereafter, the respective raw materials are frozen into desired shapes to form frozen bodies thereof. The frozen bodies thus formed are brought into contact with each other to form an assembly thereof, the assembly is exposed to a condition under which the frozen bodies begin to melt, and the assembly is then freeze-dried. Thus, a porous body having regions different in physical properties can be obtained. Such a porous body can be used as, for example, an adhesion inhibitory material or a scaffold for a cell culture.

19 Claims, 4 Drawing Sheets

U.S. PATENT DOCUMENTS

2003/0236573 A1* 12/2003 Evans et al. .............. 623/23.58
2007/0009585 A1* 1/2007 Morinaga et al. .......... 424/445

FOREIGN PATENT DOCUMENTS

| | | |
|---|---|---|
| JP | 2-268766 | 11/1990 |
| JP | 6-157807 | 6/1994 |
| JP | 10-234844 | 9/1998 |
| JP | 2001-026664 | 1/2001 |
| JP | 2001-049018 | 2/2001 |
| JP | 2001-212225 | 8/2001 |
| JP | 2002-541925 | 12/2002 |
| JP | 2003-508128 | 3/2003 |
| JP | 2003-102755 | 4/2003 |
| WO | 00/62829 | 10/2000 |
| WO | 01/15751 | 3/2001 |

* cited by examiner

PROCESS FOR PRODUCTION OF POROUS BODY AND USES THEREOF

TECHNICAL FIELD

The present invention relates to processes for producing porous bodies, particularly those useful as, for example, adhesion inhibitory materials or cell scaffolds in medical fields directed to tissue engineering and regenerative medical engineering.

BACKGROUND ART

In the fields of, for example, regenerative medical engineering and tissue engineering, there are attempts to use various artificial materials as adjunctive materials for treatments or biological tissue replacements. Specific examples that actually have been put to practical use include an adhesion inhibitory material for preventing tissues from adhering to each other in surgical treatment as well as a scaffold for a cell culture, a biological tissue replacement, an artificial blood vessel, and an artificial trachea in regenerative medicine.

Such artificial materials used widely are, for example, polymer porous bodies. The polymer porous bodies can be produced by, for example, freeze-drying polymer solutions (Patent Documents 1 to 4). However, even among porous bodies formed of polymers in the same manner, they are required to have various properties and functions according to, for example, application sites in biological bodies and intended uses thereof.

The adhesion inhibitory material is placed on, for example, the surface of a tissue to be protected (for example, a damaged area) in the patient body. It is intended not to prevent the tissue to be protected from healing and is intended to prevent adhesion between the tissue to be protected and the surrounding tissue during the healing period. In order to fulfill this function satisfactorily, first of all, it is desirable that in the adhesion inhibitory material, the surface to be brought into contact with the tissue to be protected have excellent cell invasiveness. This improves adhesiveness between the adhesion inhibitory material and the tissue to be protected and thereby makes it possible to omit, for example, suturing. On the other hand, it is desirable that in the adhesion inhibitory material, the surface to be brought into contact with the surrounding tissue have, for example, less cell invasiveness. This can prevent cells of the surrounding tissue from invading the adhesion inhibitory material and adhering to the tissue to be protected. As described above, when the artificial porous body is used as an adhesion inhibitory material, for example, the surface to be brought into contact with a tissue to be protected and the opposite surface thereto (the surface to be brought into contact with a tissue that may adhere to the aforementioned tissue) are required to be completely different in property, function, and structure from each other.

Furthermore, there also are materials that are required to have excellent cell and substance invasiveness in both surfaces of the porous bodies depending on the intended uses thereof, which are different from the adhesion inhibitory material. Examples thereof include artificial blood vessels and artificial tracheae. A biological blood vessel has a three-layer membrane structure including an intima formed of endothelial cells, a tunica media formed mainly of smooth muscles, and an adventitia rich in connective tissues. Generally, the intima and adventitia serve in, for example, exchange of substances between blood and the external tissues. Furthermore, the adventitia also serves to maintain a blood vessel so as to prevent it from excessively dilating to rupture when, for example, the blood pressure increases. Moreover, the tunica media provides flexibility that copes with, for example, dilatation and constriction of the blood vessel. In this manner, since the respective parts provide specific functions, for example, the intima needs to have material permeability and blood compatibility, the tunica media flexibility, and the adventitia material permeability and physical strength, as their properties, respectively. Accordingly, artificial blood vessels also are required to have such properties as described above that are different from one another in the respective parts. However, since a porous body with good material permeability commonly has a large number of pores per area and also has a pore size that increases depending on the type of the substance to be permeated, it also has a problem of insufficient strength at the same time. Therefore, in order to avoid this problem, the external part of the porous body needs to have sufficiently high strength.

Furthermore, in order selectively to allow a specific cell to, for example, migrate, engraft, and proliferate according to the intended use, there is a demand for a material that allows specific cells to permeate and a material that does not allow cells to permeate but allows only substances such as nutrition and oxygen to permeate. In order to exhibit such selectivity, it is considered that a porous body with composite regions that are different in property and structure is desirable as compared to a porous body with uniform properties and structure.

As described above, the porous body is required to exhibit desired properties in desired positions according to the intended use thereof. Generally, however, available porous materials are homogeneous materials. Moreover, the process for controllably producing, for example, one whose opposed surfaces are different in property from each other or one whose inner part has different properties, according to need, has not been known. Accordingly, at present, it is necessary to prepare a plurality of porous materials that are different in property from each other beforehand and to laminate them in a desired order to form a porous body (Patent Documents 5 to 8). Furthermore, when a plurality of porous materials are laminated, it is desired that the respective layers adhere closely to one another and the resultant porous body be a unified product as a whole. However, with respect to polymer porous materials, the method of allowing a plurality of members to adhere to one another that has been reported is only a method of allowing them to adhere to one another with an adhesive such as a solvent (Patent Document 9). In the case of such a method, the process of producing a porous body requires an adhesion step additionally. Furthermore, safety of the adhesive and the residue thereof as well as adhesiveness between porous materials emerge as problems.

[Patent Document 1] JP 10 (1998)-234844 A
[Patent Document 2] JP 2001-49018 A
[Patent Document 3] JP 2002-541925 A
[Patent Document 4] JP 02 (1990)-2659935 A
[Patent Document 5] U.S. Pat. No. 5,607,474 A
[Patent Document 6] JP 2003-508128 A
[Patent Document 7] JP 2003-102755 A
[Patent Document 8] JP 02 (1990)-2659935 A
[Patent Document 9] U.S. Pat. No. 5,514,378 A

DISCLOSURE OF INVENTION

Therefore, the present invention is intended to provide a process for producing a porous body with different physical properties in desired regions by a new technique and not by a method of bonding two or more porous materials that have been made porous beforehand to each other with, for example, an adhesive as in the conventional manner.

A process for producing a porous body of the present invention is a process for producing a porous body with different physical properties in desired regions and is characterized by including the following steps (A) to (D):
(A) providing at least two raw materials having different compositions, each of which contains a polymer and a solvent,
(B) freezing the respective raw materials into desired shapes to form frozen bodies of the respective raw materials,
(C) forming an assembly of the frozen bodies, where at least one of the following steps (C1) and (C2) is included,
 (C1) forming the assembly of the frozen bodies and then exposing the assembly to a condition under which the frozen bodies begin to melt, and
 (C2) exposing the respective frozen bodies to a condition under which the frozen bodies begin to melt and then forming the assembly of the frozen bodies, and
(D) freeze-drying the assembly after step (C) to form a porous body.

A porous body of the present invention is characterized by being obtained by the process of the present invention, and a biomaterial of the present invention is characterized by including a porous body of the present invention.

The present invention makes it possible to obtain a porous body with different physical properties in desired regions without bonding materials that have been made porous beforehand to each other. Generally, the physical properties of the porous materials depend on the raw material compositions thereof or the methods of preparing them if the freeze-drying conditions are fixed. The inventors found a process in which a plurality of raw materials were prepared that would exhibit desired physical properties by being made porous and the frozen bodies thereof were used prospectively. That is, as described above, the porous body is required to have different physical properties in respective regions according to the intended use thereof. Therefore, the inventors conceived of a process in which frozen bodies in desired forms (for example, shape and thickness) of the respective raw materials were produced first and the respective frozen bodies were placed so that physical properties depending on the respective raw materials were located in desired regions when they were made porous, to form an assembly of the frozen bodies. Accordingly, when it finally is subjected to a pore forming treatment (freeze-drying treatment), the resultant porous body has the desired physical properties in desired regions. Furthermore, the inventors conceived of releasing the frozen state of the frozen bodies or the assembly of the frozen bodies prior to the pore forming treatment. That is, when the assembly of the frozen bodies is formed after the frozen bodies are exposed to the condition under which the frozen bodies begin to melt, components of the respective raw materials are mixed together in the portion where the frozen bodies are in contact with each other, which results in no boundary between the two. Furthermore, when the assembly is exposed to the condition under which the frozen bodies begin to melt, the portion where the frozen bodies are in contact with each other begins to melt and thereby components of the respective raw materials are mixed together, which results in no boundary between the two. Therefore, successively, the assembly is subjected to a pore forming treatment by freeze-drying, and thereby a porous body having desired physical properties for respective regions can be obtained. The porous body thus obtained is in a state where porous layers derived from the respective frozen bodies are unified as a whole, which is different from the conventional one. Furthermore, according to the present invention, it is sufficient to carry out the time-consuming freeze-drying treatment only once for producing one porous body and thereby the production time can be shortened. Moreover, the present invention also makes it possible to vary the physical properties, for example, continuously, discontinuously, or by phases. Such a production process makes it possible to produce various porous bodies through one freeze-drying treatment merely by changing the composition ratio of the raw materials and arranging the frozen bodies having the desired shapes. Accordingly, the production process of the present invention is a very useful technique particularly for providing biomaterials to be used in medical fields such as those described above.

DESCRIPTION OF THE PREFERRED EMBODIMENTS

Figure 1:
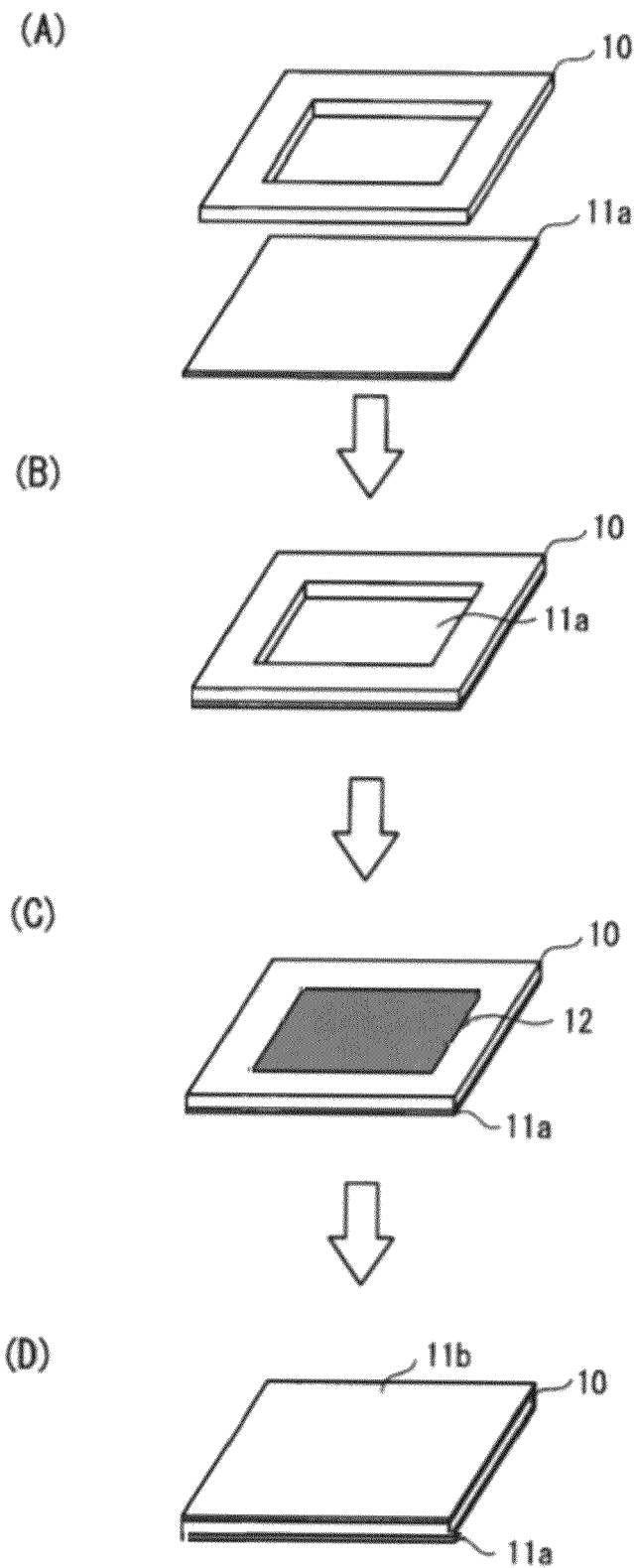
FIG. 1 is a schematic view showing an example of the steps for forming a frozen body of a raw material in one embodiment of the present invention.

As described above, the production process of the present invention is a process for producing a porous body with different physical properties in desired regions and is characterized by including the following steps (A) to (D):
(A) providing at least two raw materials having different compositions, each of which contains a polymer and a solvent,
(B) freezing the respective raw materials into desired shapes to form frozen bodies of the respective raw materials,
(C) forming an assembly of the frozen bodies, where at least one of the following steps (C1) and (C2) is included,
 (C1) forming the assembly of the frozen bodies and then exposing the assembly to a condition under which the frozen bodies begin to melt, and
 (C2) exposing the respective frozen bodies to a condition under which the frozen bodies begin to melt and then forming the assembly of the frozen bodies, and
(D) freeze-drying the assembly after step (C) to form a porous body.

The polymer of the present invention is not limited and can be selected suitably according to, for example, the intended use. As described above, the porous body of the present invention can be used conceivably, for example, in vivo. Therefore, in that case, the polymer is preferably a material with excellent safety with respect to biological bodies or a material having excellent compatibility with biological bodies. Furthermore, when the porous body of the present invention is used for applications in which, for example, it exhibits the effect thereof in vivo for a certain period of time and it is no longer required after achieving the purpose thereof as in the case of an adhesion inhibitory material, the polymer is preferably a polymer (bioabsorbable polymer) that eventually is decomposed and absorbed in vivo.

The polymer can be, for example, either a homopolymer (for example, a condensation polymer) composed of identical monomers or a copolymer composed of at least two types of monomers. The copolymer may be any one of, for example, a random polymer, a block polymer, a graft copolymer, and an alternating copolymer.

Examples of the copolymer include a lactide-caprolactone copolymer composed of lactide and caprolactone, a lactide-glycolic acid copolymer, a trimethylene carbonate-lactide-glycolide copolymer composed of trimethylene carbonate, lactide, and glycolic acid, and a glycolic acid-caprolactone copolymer. Examples of the homopolymer include polylactic acid, which is a polycondensate of lactic acid, polyglycolic acid, which is a polycondensate of glycolic acid, and poly-β-hydroxybutyric acid (poly-β-butyrolactone) composed of β-hydroxybutyric acid.

Particularly, preferable examples of a polymer with excellent safety and compatibility with respect to biological bodies include a lactide-caprolactone copolymer, polyethylene, polyvinyl alcohol (PVA), and hydroxyethyl hexamethylene methacrylate (HEMA). Furthermore, preferable examples of the bioabsorbable polymer include a lactide-caprolactone copolymer, polylactic acid, a lactide-glycolic acid copolymer, a trimethylene carbonate-lactide-glycolide copolymer composed of trimethylene carbonate, lactide, and glycolic acid, and a glycolic acid-caprolactone copolymer. In the present invention, any one of the polymers may be used or two or more of them may be used in combination.

The molecular weight (weight-average molecular weight) of the polymer is not limited and is, for example, 5,000 to 2,000,000, preferably 10,000 to 1,500,000, and more preferably 100,000 to 1,000,000.

A lactide-caprolactone copolymer is described below as an example of the polymer of the present invention. However, the polymer of the present invention is not limited thereto. In the copolymer, the molar ratio between lactide and caprolactone is, for example, in the range of 90:10 to 10:90, preferably in the range of 85:15 to 20:80, more preferably in the range of 80:20 to 40:60. The molecular weight (weight-average molecular weight) of the copolymer is, for example, 5,000 to 2,000,000, preferably 10,000 to 1,500,000, and more preferably 100,000 to 1,000,000.

The process for preparing the copolymer is not particularly limited, and a conventionally known process can be used. Generally, lactide and caprolactone that are used as starting raw materials may be copolymerized through ring-opening polymerization, or lactide (a cyclic dimer of lactic acid) may be synthesized from lactic acid and then may be copolymerized with caprolactone. Furthermore, the method of synthesizing lactide using lactic acid also is not particularly limited and a conventionally known method can be used. The lactide is not particularly limited and L-lactide, D-lactide, or a mixture (D,L-lactide) thereof can be used. L-lactic acid, D-lactic acid, or a mixture (D,L-lactic acid) thereof can be used as lactic acid. As described above, when lactic acid is used as a starting raw material, it is preferable that a monomer lactic acid be converted to a dimer lactide and the molar ratio of the lactide thus converted and caprolactone be in the aforementioned range. Examples of lactone include ε-caprolactone, γ-butyrocaprolactone, and δ-valerocaprolactone. Particularly, ε-caprolactone is preferable. The lactide-caprolactone copolymer further may contain, for example, another copolymerization component composing a bioabsorbable polymer as a component thereof in addition to lactide and caprolactone. Examples of such a component include glycolic acid, trimethylene carbonate, β-hydroxybutyric acid, protein, and a copolymer polymerization component derived from a sugar chain.

In the present invention, the solvent that is used for preparing a raw material (also referred to as a "raw material preparation solvent") is not limited and various solvents can be used. According to the type of the solvent, for example, the pore diameter and strength of the porous body finally formed can be adjusted. Specific examples of the solvent are described later.

Next, the process for producing a porous body of the present invention is described using an example in which a lactide-caprolactone copolymer is employed as a polymer.

(A) Preparation of Raw Material

In the present invention, first, at least two types of raw materials having different compositions from each other are prepared. In formation of a porous body by freeze-drying, physical properties such as diameters of pores to be formed, porosity, strength, thickness, material permeability, and adhesiveness (for example, adhesiveness to a target biological tissue) can be adjusted by, for example, varying the compositions of the raw materials if the freeze-drying conditions are the same. In the present invention, as described later, the respective raw materials may be subjected to, for example, a freeze-drying treatment simultaneously under the same conditions. In this case, a change in the compositions of the raw materials or in the process for preparing them allows the physical properties to be adjusted into various physical properties that depend on the respective raw materials. With respect to the compositions of the raw materials, for example, the type of the polymer to be used may be changed or the ratio of the polymer to be added may be changed. Furthermore, the type of the solvent to be used may be changed, or when a mixture of at least two types of solvents is used as the raw material preparation solvent, the ratios of the solvents to be added may be changed. Moreover, the present invention is not characterized in that the raw materials are allowed to have certain compositions to change the physical properties into certain types. The present invention is characterized primarily by using respective frozen bodies of a plurality of raw materials having different compositions from each other, exposing an assembly (C1) that has been formed or frozen bodies (C2) before an assembly is formed to a condition under which the frozen bodies begin to melt, and then subjecting the assembly to a freeze-drying treatment.

Examples of the raw materials include a solution containing the lactide-caprolactone copolymer dissolved in the aforementioned solvent (hereinafter also referred to as a "solution raw material") as well as a gelled product (hereinafter also referred to as a "gel raw material") of a lactide-caprolactone copolymer gelled with the solvent. Such a raw material in the solution state and a raw material in the gelled state can be made porous by a freeze-drying treatment described later. Accordingly, the preferable type of the solvent is, for example, a solvent that dissolves the aforementioned copolymer or a solvent that gels the copolymer. Hereinafter, the solution raw material and the gel raw material are described.

[Solution Raw Material]

The raw material preparation solvent in which the aforementioned polymer is dissolved is not limited in type as long as it can dissolve the polymer. Examples thereof include a solvent having solubility to the polymer (hereinafter also referred to as a "good solvent") and a mixture of the good solvent and a solvent having insolubility to the polymer (hereinafter also referred to as a "poor solvent"). Examples of the good solvent include 1,4-dioxane, dimethyl carbonate, chloroform, and acetone. Any one of them may be used or two or more of them may be used in combination. Furthermore, the poor solvent is preferably a solvent having compatibility with the good solvent, and examples thereof include water, ethanol, tertiary butyl alcohol, and hexane. Any one of them may be used or two or more of them may be used in combination. A preferable combination of a good solvent and a poor solvent is, for example, a combination of 1,4-dioxane and water.

Similarly with respect to polymers other than the lactide-caprolactone copolymer, the solvent is not particularly limited. Specifically, for example, polylactic acid (PLA) allows the same solvents as those used for, for example, the lactide-caprolactone copolymer to be used, and examples of the combination thereof also can be the same. Furthermore, with respect to polyglycolic acid (PGA), a preferable example of the good solvent is hexafluoroisopropanol (1,1,1,3,3,3-hexafluoro-2-propanol), and preferable examples of the poor solvent include hexane, chloroform, and ethers.

Generally, the polymer is dissolved or gelled according to the ratio of the good solvent and the ratio of the poor solvent (particularly, the ratio of the poor solvent) in the raw material preparation solvent. Therefore, when the polymer is to be dissolved, preferable ratios thereof to be added are as follows, for example. However, the following conditions are examples and the present invention is not limited thereto. For instance, when 4 parts by weight of the polymer is dissolved in 96 parts by weight of the preparation solvent at 25° C., the ratio of the good solvent to be added in a raw material (100 wt %) finally obtained is set, for example, preferably at a ratio exceeding 84.48 wt % and more preferably at least 83.52 wt %. The upper limit of the ratio of the good solvent to be added is not limited and is, for example, 96 wt %. Furthermore, for example, the ratio of the poor solvent to be added in the raw material (100 wt %) finally obtained is set, for example, preferably in the range of 12 to 40 wt % and more preferably in the range of 12 to 16 wt % under the same conditions. The lower limit of the ratio of the poor solvent to be added is not limited and is, for example, 0 wt %. Changing the ratios of the good solvent and the poor solvent in the aforementioned ranges can change, for example, the diameter sizes of pores to be formed, porosity, strength, thickness, material permeability, and adhesiveness. Furthermore, the present invention is not limited to those conditions, and for example, the ratio of the poor solvent may be in the range of at least 0 but less than 12 wt % under the same conditions.

The solution raw material can be prepared by, for example, dissolving the copolymer in a raw material preparation solvent described above. In this solution raw material (100 wt %), the ratio of the copolymer to be added is not limited. The lower limit thereof is, for example, at least 0.1 wt %, preferably at least 2 wt %, and more preferably at least 3 wt %. The upper limit thereof is, for example, 24 wt % or lower, preferably 8 wt % or lower, and more preferably 5 wt % or lower. Furthermore, the weight ratio between the copolymer and the good solvent is preferably, for example, (4:96) to (3.52:84.48). The weight ratio between the copolymer and the poor solvent is preferably, for example, (4:0) to (3.52:12).

[Gel Raw Material]

The gel raw material can be prepared by, for example, the following steps (A1) to (A3). In the following step (A2), the separation between the liquid phase and the gel phase can be judged, for example, visually. Furthermore, in the following step (A3), for example, the gel phase does not need to be recovered exclusively and, for example, the liquid phase (raw material preparation solvent) may be present due to operational reasons.

(A1) Mixing the polymer and the solvent to prepare a mixture (A2) Allowing the mixture to stand and thereby separating a liquid phase and a gel phase from each other (A3) Recovering the gel phase as the gelled product With respect to the raw material preparation solvent for gelling the polymer, the type thereof is not limited as long as it can gel the polymer. Examples thereof include the aforementioned mixture of a good solvent and a poor solvent. Examples of the good solvent and the poor solvent include those described above. A preferable example of the combination of the good solvent and the poor solvent is a combination of 1,4-dioxane and water.

As described above, the polymer generally is dissolved or gelled depending on the ratios of the good solvent and the poor solvent (particularly the ratio of the poor solvent) in the raw material preparation solvent. Therefore, when the polymer is intended to be gelled, for example, the following ratios thereof to be added are preferable. However, the following conditions are examples and the present invention is not limited thereto. When 4 parts by weight of the polymer is mixed with 96 parts by weight of the preparation solvent to be gelled at 25° C., it is preferable that in the mixture (100 wt %) used in step (A1), the ratio of the poor solvent to be added be set at, for example, 12 wt % or more. The upper limit of the ratio of the poor solvent to be added is not limited and is, for example, 40 wt % or lower and preferably 35 wt % or lower. Furthermore, it is preferable that, for example, in the mixture (100 wt %), the ratio of the good solvent to be added be set at, for example, 84.48 wt % or lower under the same conditions. The lower limit of the ratio of the good solvent to be added is not limited but is at least 57.6 wt % and more preferably at least 62.4 wt %.

In the mixture (100 wt %), the ratio of the copolymer to be added is not limited. The lower limit thereof is, for example, at least 0.1 wt %, preferably at least 2 wt %, and more preferably at least 3 wt %. The upper limit thereof is, for example, 24 wt % or lower, preferably 8 wt % or lower, and more preferably 5 wt % or lower. Furthermore, the weight ratio between the copolymer and the good solvent is preferably, for example, (3.52:84.48) to (2.4:57.6). The weight ratio between the copolymer and the poor solvent is preferably, for example, (3.52:12) to (2.4:40).

When the solution raw material and the gel raw material are freeze-dried under the same conditions, they exhibit, for example, the following different physical properties from each other. As compared to the porous material derived from the gel raw material, the porous material derived from the solution raw material has, for example, a relatively larger pore diameter and a relatively higher porosity. In the case of such physical properties, for example, since cells tend to invade the porous material, the porous material derived from the solution raw material is suitable for the portion to serve as a scaffold for cells or a tissue. On the other hand, as compared to the porous material derived from the solution raw material, the porous material derived from the gel raw material has, for example, a relatively higher strength even in the case of the same thickness, a relatively smaller pore diameter, and a relatively lower porosity. In the case of such physical properties, for example, cells tend not to invade the porous material but nutrient and air can be transmitted, and therefore the porous material derived from the gel raw material is suitable, for example, for a portion for preventing adhesion with cells or tissues. Accordingly, in the present invention, when the treatment as described later is performed using such a solution raw material and a gel raw material, a porous body can be formed that is provided, for example, with physical properties suitable for a scaffold for cells or a tissue by using the solution raw material in a certain region and with physical properties that has suitable strength and that is suitable for preventing adhesion of cells or tissues by using the gel raw material in another region.

As described above, the physical properties provided when the solution raw material and the gel raw material are used are described as one example, but the present invention is not limited thereto. For instance, the use of two or more types of solution raw materials also can provide different physical properties. That is, the physical properties (for example, pore diameter, porosity, strength, thickness, material permeability, and adhesiveness) obtained when the solution raw materials are made porous also can be changed depending on the type of the polymer and the ratio of the polymer to be added in each solution raw material as well as the ratios of the good solvent and the poor solvent to be added (particularly, the ratio of the poor solvent to be added) in the raw material preparation solvent. Furthermore, different physical properties also can be provided by using, for example, two or more types of gel raw materials. That is, the physical properties obtained when the gel raw materials are made porous also can be changed depending on the type of the polymer and the ratio of the polymer to be added in each gel raw material as well as the ratios of the good solvent and the poor solvent to be added in the raw material preparation solvent. Moreover, even in the case of using the same polymer, the physical properties of the porous material are changed by, for example, changing the ratio of the polymer to be added or the composition of the raw material preparation solvent. Accordingly, for example, a porous material can be obtained that is formed of the same material and has regions with different physical properties.

Specifically, for example, in the case of using a solution raw material, an increase in the ratio of the poor solvent in the raw material preparation solvent results in changes in physical properties of the resultant porous body, for example, a decrease in porosity, a reduction in pore size, an increase in strength, and a deterioration in material permeability. Furthermore, in the case of using the gel raw material, an increase in the ratio of the poor solvent in the raw material preparation solvent results in changes in physical properties of the resultant porous body, for example, a decrease in porosity, almost no change in pore size, and an increase in strength.

(B) Freezing of Respective Raw Materials

Next, the respective raw materials are frozen into desired shapes and thereby frozen bodies of the respective raw materials are formed. The shapes of the frozen bodies can be set to desired shapes by using, for example, forming dies.

For example, the shapes of the regions derived from the respective raw materials in the porous body finally obtained can be adjusted according to the shapes of the respective frozen bodies that are formed in this step. Specifically, the thicknesses of the porous regions derived from the respective raw materials in, for example, the porous body finally obtained can be adjusted according to the thicknesses of the respective frozen bodies. The thicknesses of the frozen bodies can be adjusted by, for example, casting a raw material up to desired height (thickness) in a forming die. For example, in the porous body finally obtained, when the thickness of a porous region derived from a certain raw material is intended to be set to about 200 µm, the raw material can be cast up to a height (thickness) of about 200 µm in a forming die in this step to form a frozen body. This makes it possible to adjust the thickness of the porous region derived from the aforementioned raw material to about 200 µm in the porous body finally obtained. Furthermore, the thickness of the porous body finally obtained also can be adjusted by changing the composition of the raw material preparation solvent. Specifically, a relatively reduced ratio of the poor solvent in the raw material can result in a relatively reduced thickness of the resultant porous body. On the other hand, a relatively increased ratio of the poor solvent in the raw material can result in a relatively increased thickness of the resultant porous body. In this manner, when the ratio of the poor solvent in the raw material is changed, the thickness of the porous body finally obtained can be adjusted in the range of, for example, about 100 to 200 µm by, for example, casting the raw material up to a height (thickness) of about 200 µm in the forming die to form a frozen body. As described above, since the thickness can be adjusted very easily, it also is easy to form the porous body into a thin film and to form the respective regions into thin layers.

The freezing temperature is not limited as long as it is a temperature at which the respective raw materials freeze. A preferable specific example is equal to or lower than the eutectic point temperature of the raw material (for example, a mixture of a polymer and a solvent). Generally, the aforementioned eutectic point denotes the temperature at which a mixture of at least two types of substances is crystallized. The aforementioned temperature is, for example, lower than 0° C., preferably lower than −10° C., and more preferably −50° C. to −10° C. The freezing treatment time is not limited and can be set suitably according to, for example, the amount of each raw material and the height (thickness) of the raw material that is cast into a forming die. When the thickness of the raw material cast into the forming die is, for example, about 200 to 500 µm, it can be allowed to stand for 30 to 60 seconds under the aforementioned temperature condition.

An example of formation of the above-mentioned frozen body is described below using FIG. 1. FIG. 1 is a schematic view showing the steps for forming a frozen body using a forming die. However, this is an example and does not limit the present invention.

As shown in FIG. 1(A), first, a frame-shaped forming die 10 and a plate-like body 11a are provided. The shape of the forming die 10 shown in FIG. 1(A) is a rectangular frame shape but is not limited thereto. Preferably, the height of the forming die 10 is adjusted to, for example, the desired thickness of the frozen body. The material of the forming die 10 is not particularly limited. Preferably, it is made of, for example, metal due to its excellent heat conduction. Furthermore, the plate-like body 11a is not particularly limited but a sheet made of fluororesin such as polytetrafluoroethylene is preferable because it is separated easily from the frozen body later.

Subsequently, as shown in FIG. 1(B), the forming die 10 is placed on the plate-like body 11a. In this stage, it is preferable that no gap exist between the plate-like body 11a and the forming die 10. Thereafter, as shown in FIG. 1(C), a raw material 12 is cast into the forming die 10 placed on the plate-like body 11a. In this stage, it is preferable that the raw material 12 be cast up to the upper open face of the forming die 10 so that the inside of the forming die 10 is filled therewith. When this technique is employed, as described above, since the height of the forming die 10 has been set to be equal to the desired thickness of the frozen body, the thickness of the frozen body to be formed can be adjusted easily. Since the thickness can be adjusted through casting as described above, it also is possible to make the frozen body, for example, very thin, for example, into a thin film shape with a thickness of 1 mm or less. Subsequently, as shown in FIG. 1(D), the upper open face of the forming die 10 further is covered with a plate-like body 11b and then a freezing treatment is performed. In this case, since the frozen body to be formed through the freezing treatment is supported in the vertical direction by the plate-like bodies 11a and 11b, the shape of the frozen body can be maintained. This allows the frozen body to be handled very easily before and after the freezing treatment.

(C1) Formation of Assembly of Frozen Bodies and Release of Frozen State

Subsequently, the frozen bodies are brought into contact with each other and thereby an assembly of the frozen bodies is formed. In this step (C1), the shape of the assembly is not limited. The shape of the assembly and the regions where the frozen bodies are placed can be determined according to, for example, the intended use of the porous body. Therefore, examples thereof include an assembly with the frozen bodies laminated in the thickness direction and an assembly with the frozen bodies brought into contact with each other in parallel in the plane direction. When a porous body of the present invention is used as a biomaterial, it is preferable that an assembly be formed in which, for example, frozen bodies are laminated in the thickness direction. The present invention makes it possible to laminate, for example, a desired number of frozen bodies with desired thickness in the desired order.

As described above, the shape of the assembly is not limited. This embodiment is described using an example in which respective frozen bodies are laminated together to form a laminate of the frozen bodies.

Preferably, the frozen bodies are laminated, with the shapes of the respective frozen bodies being maintained. The temperature condition for the lamination treatment is not limited. However, since it is desirable that the shapes of the frozen bodies be maintained, it is preferable that the lamination treatment be performed, for example, under the temperature condition for the freezing treatment performed in step (B). In this step, the expression "maintaining the shapes of the frozen bodies" embraces, with respect to the frozen bodies, not only perfectly maintaining the frozen state at the end of step (B) but also maintaining, for example, the shapes that allow them to be handled in the lamination treatment. Accordingly, even in the case where the respective frozen bodies have begun to melt at the time of lamination, this is acceptable as long as the lamination treatment is possible.

Figure 2:
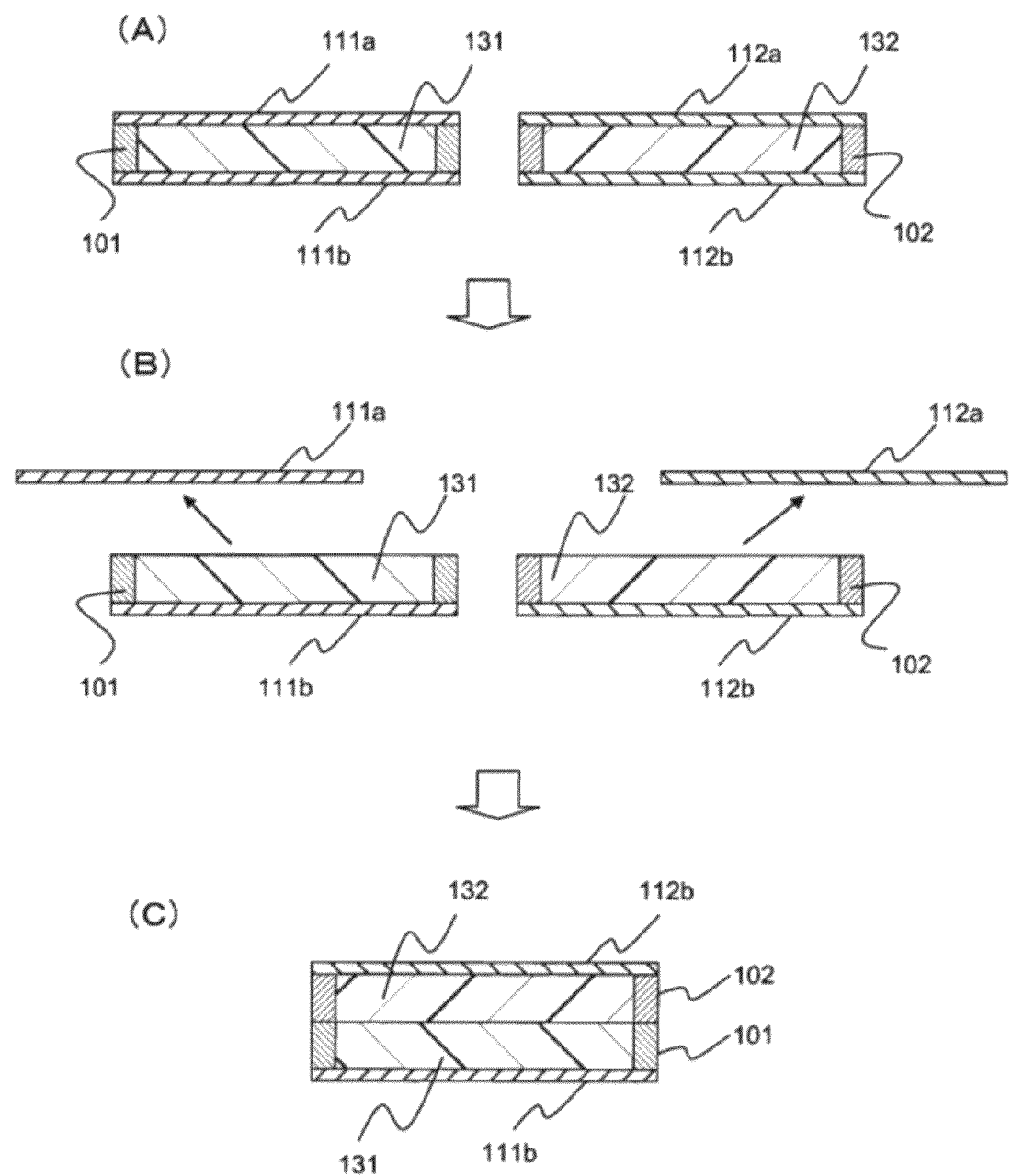
FIG. 2 is a schematic view showing an example of the steps for laminating frozen bodies of raw materials in another embodiment of the present invention.

An example of steps for laminating two frozen bodies is described below using FIG. 2. FIG. 2 is a schematic view showing steps for laminating frozen bodies formed in FIG. 1.

First, as shown in FIG. 2(A), two frozen bodies (131 and 132) are prepared in the same manner as shown in FIG. 1. The two frozen bodies (131 and 132) are present inside frame-shaped forming dies (101 and 102), each of which has plate-like bodies (111a and 111b, 112a and 112b) on both sides thereof, respectively. Subsequently, the plate-like bodies (111a and 112a) located on one side are separated as shown in FIG. 2(B). This results in a state where one surface of each of the frozen bodies (131 and 132) inside the forming dies (101 and 102) is exposed. Thereafter, as shown in FIG. 2(C), the two frozen bodies (131 and 132) are laminated together so that the exposed surfaces of the frozen bodies (131 and 132) come into contact with each other.

Subsequently, the assembly is exposed to the condition under which the frozen bodies begin to melt. This allows the respective frozen bodies to begin to melt and thereby the portion where the frozen bodies are in contact with each other is brought into a state where the compositions of the two are mixed together. Accordingly, when the assembly is subjected to a freeze-drying treatment in the next step, a porous body can be obtained in which boundary portions of the respective layers have been blended together.

In the present invention, the expression "the condition under which the frozen bodies begin to melt" can be described as, for example, the temperature condition under which the frozen states of the frozen bodies are released and embraces a temperature condition exceeding the melting points and a temperature condition exceeding the eutectic points. Furthermore, in the present invention, the expression "the condition under which the frozen bodies begin to melt" embraces, for example, a condition where the shapes that allow the assembly in step (C1) or the frozen bodies in step (C2) to be handled are maintained, as described above.

This treatment can be carried out by, for example, exposing the laminate under a temperature condition of at least the highest melting point among those of the respective frozen bodies composing the assembly. Furthermore, it can be carried out by exposing the laminate to a temperature exceeding the highest eutectic point among those of the respective raw materials (a mixture of a polymer and a solvent) forming the respective frozen bodies. Specific examples of the temperature are, for example, at least −10° C., preferably 0 to 25° C., and more preferably 10 to 20° C. The treatment time is not limited, but, for example, when the treatment is carried out at 25° C., the treatment time is preferably at least 30 seconds and more preferably 60 seconds. The upper limit thereof is not limited and is, for example, 600 seconds or less and preferably 300 seconds or less. As described above, the frozen bodies can be laminated in step (C2) instead of step (C1), with the respective frozen bodies having begun to melt. Furthermore, only the portions of the frozen bodies where they are laminated together may be melted with, for example, a heat conductor under a low temperature condition. In this case, the respective frozen bodies may be melted separately or either one of the frozen bodies to be brought into contact with each other (to be laminated) later may be melted.

(D) Freeze-Drying

Subsequently, the assembly is freeze-dried and thereby a unified porous body is formed. Specifically, for example, the assembly is made porous by being frozen (hereinafter also referred to as "refrozen") and then dried under reduced pressure. This allows a porous body including respective porous regions derived from respective raw materials to be obtained by, for example, one pore forming treatment, which is different from a laminate of porous materials in which materials that have been made porous beforehand are bonded to each other with, for example, an adhesive as in the conventional cases. Furthermore, in the porous body thus obtained, the regions derived from the respective raw materials exhibit physical properties corresponding to the compositions of the respective raw materials. Therefore, for example, in the case of a laminate, it includes regions that are different in, for example, pore diameter, porosity, strength, thickness, material permeability, and adhesiveness in the thickness direction. The freeze-drying can be carried out using, for example, a commercial freeze dryer and, for example, TF5-85ATANCS (trade name, manufactured by TAKARA Co, Ltd.) can be used.

In the freeze-drying treatment, with respect to, for example, the resultant porous body, it also is possible to equalize the pore diameter and to control the average pore size by further adjusting the cooling rate employed in refreezing. The cooling rate is, for example, 1000° C./hr or lower, preferably in the range of 3 to 1000° C./hr, more preferably in the range of 3 to 300° C./hr, further preferably in the range of 3 to 180° C./hr, and particularly preferably in the range of 5 to 180° C./hr. When such a freeze dryer as described above is used, for example, the temperature of the cooling rack thereof can be controlled so as to be decreased at a constant rate in such ranges. By adjusting the cooling rate in this manner, for example, in the aforementioned porous region derived from a solution raw material, for example, pores in a wide range of pore sizes (for example, 100 μm or larger) can be formed further uniformly.

In the present invention, step (C2) may be carried out instead of step (C1) described above. As described above, step (C2) is a step of exposing the respective frozen bodies to the condition under which the frozen bodies begin to melt and then forming the assembly of the frozen bodies. The condition is not particularly limited and examples thereof include the same temperature condition as described above. In step (B) described above, for example, when raw materials were frozen with a freezer that was set at a predetermined freezing temperature, melting caused after the frozen bodies are removed from the freezer to be laminated also can be utilized.

In this manner, a porous body of the present invention with different physical properties in desired regions can be obtained. The porous body of the present invention can be used as a biomaterial and specifically, it can be used as an adhesion inhibitory material, a scaffold used for, for example, regenerative medicine or a cell culture, an artificial trachea, or a drug delivery system material (DDS material).

Hereinafter, the present invention is described in further detail using examples but is not limited thereto.

Example 1

A porous body was produced in which the size of pores located in the opposed surfaces was different from that of pores located in the inner part.

(1) Preparation of Raw Materials for Porous Body

As described below, two types of raw materials (a raw material 1 and a raw material 2) were prepared.

First, a lactide-caprolactone copolymer (LA/CL=75/25) was prepared in which the composition ratio (molar ratio) between L-lactide and ε-caprolactone was 75:25. This copolymer (X), 1,4-dioxane (Y), and water (Z) were mixed together so that a weight ratio (X:Y:Z) of 4:96:0 (no water to be added) was obtained (the whole weight: 12 g). This mixture was a solution with the lactide-caprolactone copolymer dissolved in a solvent. This mixture was used as a raw material 1 directly for the following step. Two raw materials 1 were prepared.

On the other hand, using an identical lactide-caprolactone copolymer (LA/CL=75/25), the copolymer (X), 1,4-dioxane (Y), and water (Z) were mixed together so that a weight ratio (X:Y:Z) of 3.44:82.56:14 was obtained (the whole weight: 12 g). In this mixture, the lactide-caprolactone copolymer was gelled. Therefore, the mixture was allowed to stand and thereby to be separated into a liquid phase and a gel phase, and the gel phase was then recovered. This gel phase was used as a raw material 2 for the following step.

(2) Formation of Frozen Bodies

Next, frozen bodies were formed in accordance with FIG. 1. First, three sets were prepared, each of which included two sheets (Teflon (registered trademark) sheets, the same applies below) of 17 cm long×17 cm wide×50 μm thick and one stainless-steel forming die. The forming die had a rectangular frame shape with an internal size of 8.8 cm long×8.8 cm wide×0.26 mm deep and an external size of 17 cm long×17 cm wide×0.26 mm deep. The frame-shaped forming die was placed on the sheet and a raw material was cast up to the upper open face of the forming die so as to fill the inside of the forming die. Thereafter, the upper open face of the forming die further was covered with a sheet. In this manner, two sets of forming dies whose insides had been filled with the raw material 1 and one set of a forming die whose inside had been filled with the raw material 2 were produced.

The three sets of the forming dies described above were placed on an aluminum board that had been cooled to −80° C., with the surface of either one of the sheets facing down, and then were allowed to stand for one minute. Thus, the raw material 1 and the raw material 2 inside the forming dies were frozen. Hereinafter, the two frozen bodies of the raw material 1 are referred to as a frozen body 1a and a frozen body 1b, respectively, and the frozen body of the raw material 2 is referred to as a frozen body 2a.

(3) Lamination of Frozen Bodies

The sheet located on one side of each of the forming die set including the frozen body 1a and that including the frozen body 2a was separated therefrom, and the frozen body 1a and the frozen body 2a were laminated together, with the exposed surfaces of the respective frozen bodies being in contact with each other. Thereafter, the sheet located on the other side of the forming die including the frozen body 2a further was separated therefrom, the sheet located on one side of the frame die including the frozen body 1b was separated therefrom, and the frozen body 1b and the frozen body 2a with the frozen body 1a laminated thereon were laminated together, with the exposed surface of the frozen body 2a and the exposed surface of the frozen body 1b being in contact with each other. In this manner, a three-layer laminate was prepared in which the frozen body 1a, the frozen body 2a, and the frozen body 1b were in contact with each other in this order. Separation of the sheets and lamination of the frozen bodies were carried out under a condition of −80° C. With respect to this laminate, the one and opposite surfaces are covered with the sheets and the side faces are covered with the three forming dies stacked together.

(5) Melting

This three-layer laminate was allowed to stand for one minute under a condition of 25° C. This slightly melted the respective frozen bodies.

(6) Freeze-Drying

Subsequently, this laminate was freeze-dried with a freeze dryer (TF5-85TANCS (trade name), manufactured by TAKARA Co, Ltd.). Specifically, the cooling rack of the freeze dryer was cooled to −50° C., the sheet covering the laminate on one side was separated, and the laminate was then placed on the cooling rack, with the sheet surface located on the other side facing down. After the temperature of the cooling rack inside the freeze dryer was maintained at −50° C. for one hour, it was increased from −50° C. to 25° C. over 12 hours (at a rate of temperature rise of 6.3° C./hour) under a reduced pressure condition. When it reached 25° C., freeze-drying was completed.

The sheet located on the other side was separated, the three forming dies stacked together were removed, and thus the porous body inside them was taken out. The cross-section of this porous body was observed with a cross-section scanning electron microscope (SEMEDX TypeN (trade name), manufactured by Hitachi, Ltd.). This result is shown in FIG. 3.

Figure 3:
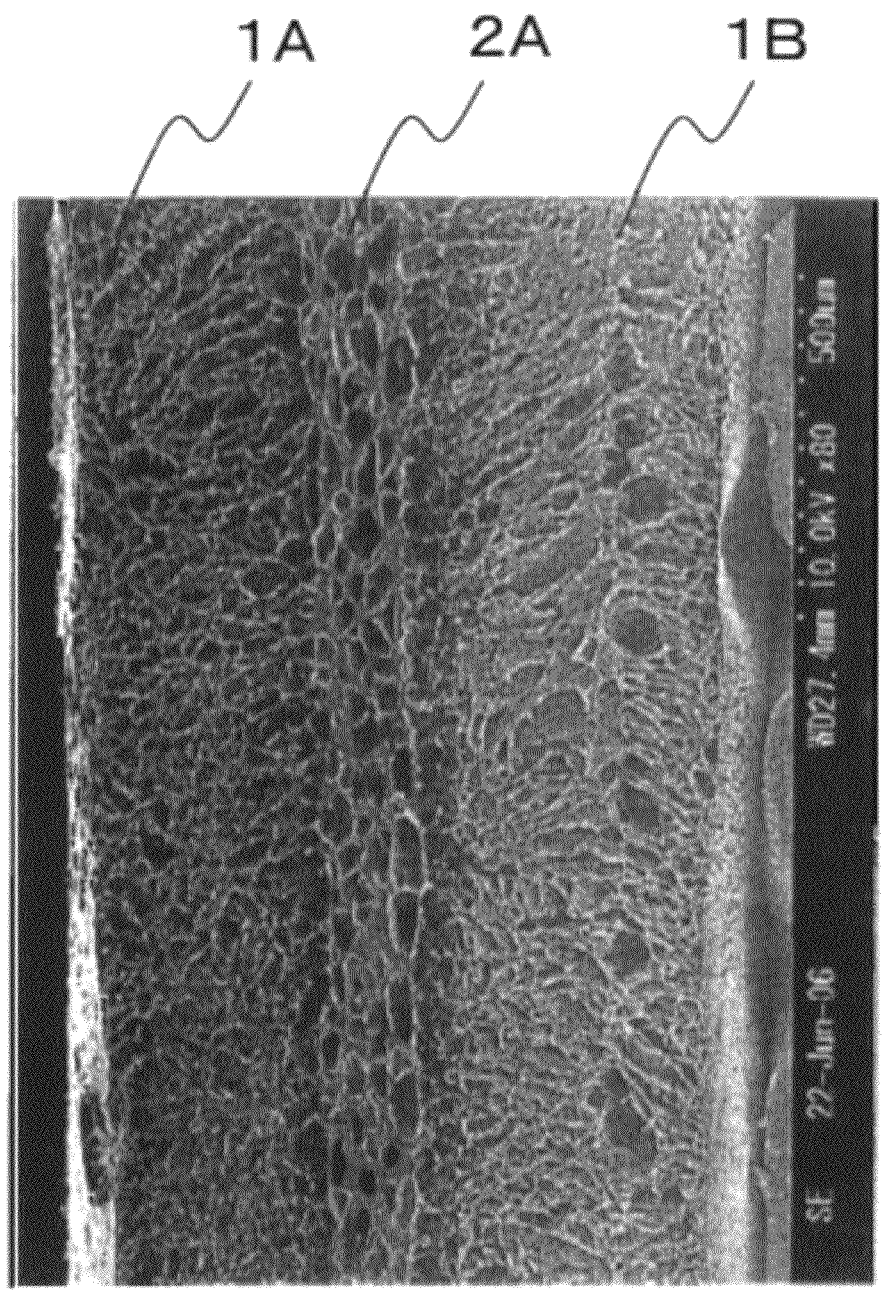
FIG. 3 is an electron micrograph showing the cross-section of a porous body according to an example of the present invention.

As shown in FIG. 3, a porous body in which three regions (1A, 2A, and 1B) that were different in pore diameters in the thickness direction were present was obtained by melting the laminate formed of the frozen body 1a, the frozen body 2a, and the frozen body 1b and then freeze-drying it. As shown in FIG. 3, it can be seen that no clear boundaries (interfaces) were present between the respective regions and the porous body was a unified product.

Example 2

(1) Preparation of Raw Materials

Using a lactide-caprolactone copolymer identical to that used in Example 1, the copolymer (X), 1,4-dioxane (Y), and water (Z) were mixed together so that a weight ratio (X:Y:Z) of 3.36:80.64:16 was obtained (the whole weight: 12 g). In this mixture, the lactide-caprolactone copolymer was gelled. Therefore, the mixture was allowed to stand to be separated into a liquid phase and a gel phase, and the gel phase was then recovered. This gel phase was used as a raw material 3 in the following step. Furthermore, a raw material 2 (a gel phase) was prepared from a mixture obtained by mixing the copolymer (X), 1,4-dioxane (Y), and water (Z) together so that a weight ratio (X:Y:Z) of 3.44:82.56:14 was obtained in the same manner as in Example 1.

(2) Formation of Frozen Bodies

Next, sets of sheets and forming dies were prepared as in Example 1. The frame-shaped forming die was placed on the sheet and a raw material was cast up to the upper open face of the forming die so as to fill the inside of the forming die. Thereafter, the upper open face of the forming die further was covered with a sheet. In this manner, one set of a forming die whose inside had been filled with the raw material 2 and one set of a forming die whose inside had been filled with a raw material 3 were produced.

The two sets of the forming dies described above were placed on an aluminum board that had been cooled to −80° C., with the surface of one sheet facing down, and were then allowed to stand for one minute. Thus, the raw material 2 and raw material 3 inside the forming dies were frozen. Hereinafter, the frozen body of the raw material 2 is referred to as a frozen body 2a and a frozen body of the raw material 3 is referred to as a frozen body 3a.

(4) Lamination

The sheet located on one side of each of the forming die set including the frozen body 2a and that including the frozen body 3a was separated therefrom, and the frozen body 2a and the frozen body 3a were laminated together, with the exposed surfaces of the respective frozen bodies being in contact with each other. In this manner, a two-layer laminate was prepared in which the frozen body 2a and the frozen body 3a were in contact with each other in this order. Separation of the sheets and lamination of the frozen bodies were carried out under a condition of −80° C. With respect to this laminate, the one and opposite surfaces are covered with the sheets and the side surfaces are covered with the two forming dies stacked together.

(5) Melting

This two-layer laminate was allowed to stand for one minute under a condition of 25° C. This slightly melted the respective frozen bodies, and the frozen bodies were unified.

(6) Freeze-Drying

Subsequently, this laminate was freeze-dried with a freeze dryer (TF5-85TANCS (trade name), manufactured by TAKARA Co, Ltd.). Specifically, the cooling rack of the freeze dryer was cooled to −50° C. and the laminate was placed thereon, with the surface of one sheet covering the laminate facing down. After the temperature of the cooling rack inside the freeze dryer was maintained at −50° C. for one hour, it was increased from −50° C. to 25° C. over 12 hours (at a rate of temperature rise of 6.3° C./hour) under a reduced pressure condition. When it reached 25° C., freeze-drying was completed.

The sheets located on both sides were separated, the two forming dies stacked together were removed, and thus the porous body inside them was taken out. The cross-section of this porous body was observed with a cross-section scanning electron microscope (SEMEDX Type N (trade name), manufactured by Hitachi, Ltd.). This result is shown in FIG. 4.

Figure 4:
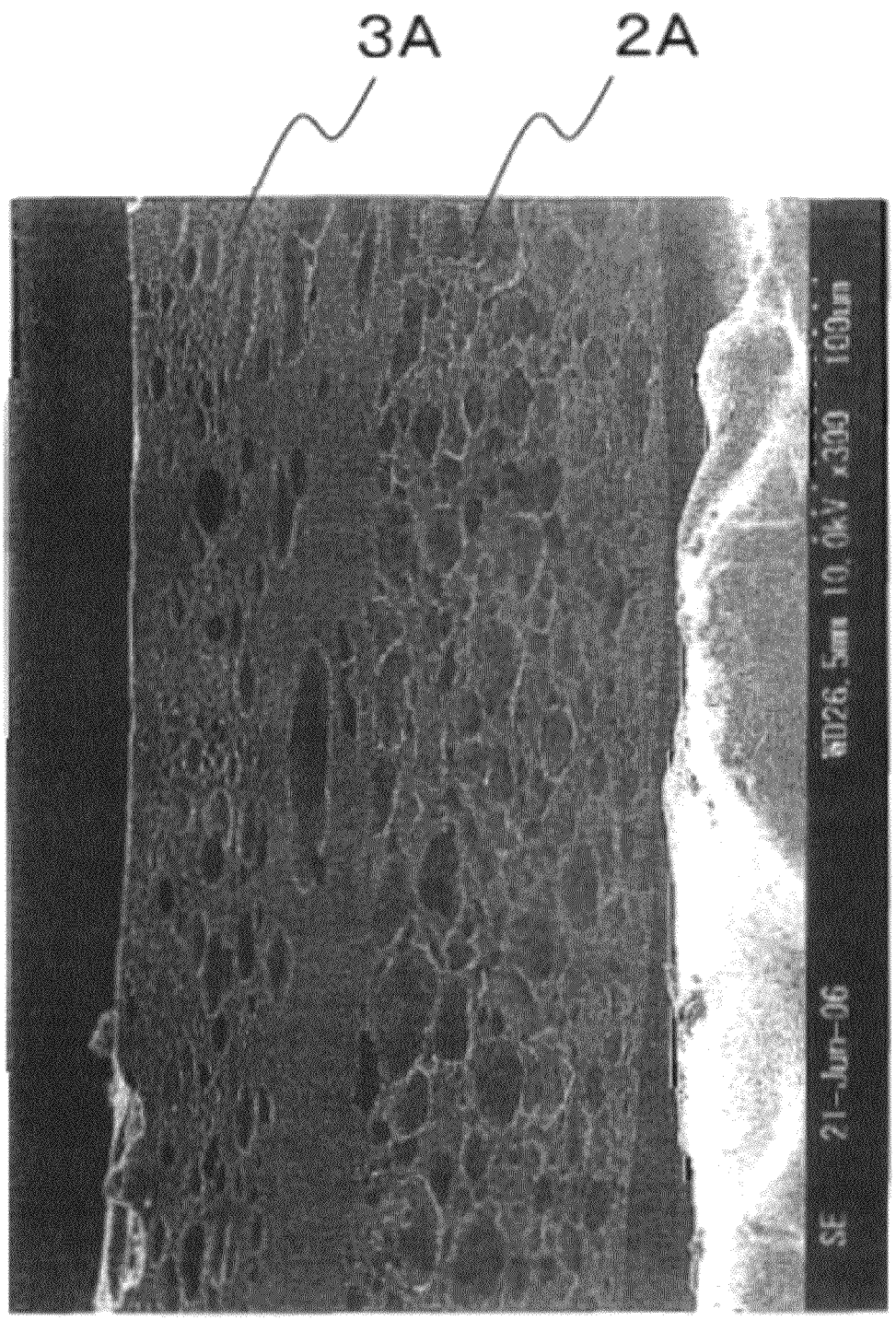
FIG. 4 is an electron micrograph showing the cross-section of a porous body according to another example of the present invention.

As shown in FIG. 4, a porous body in which two regions (2A and 3A) that were different in pore diameter were present in the thickness direction was obtained by melting the laminate formed of the frozen body 2a and the frozen body 3a and then freeze-drying it. As shown in FIG. 4, it can be seen that no clear boundary (interface) was present between the respective regions and the porous body was a unified product.

Reference Example 1

A lactide-caprolactone copolymer (P(LA/CL)), 1,4-dioxane, and water were mixed together so as to have weight ratios indicated below in the table. These mixtures were placed in vials and were then allowed to stand at 25° C., and thereby it was checked whether they were maintained in a solution state or they were separated into a liquid phase and a gel phase. As a result, Samples A to C were solutions, while Samples D to Q each were separated into a liquid phase and a gel phase.

TABLE 1

| Sample | Copolymer | Dioxane | Water |
| --- | --- | --- | --- |
| A | 4.00 | 96.00 | 0 |
| B | 3.80 | 91.20 | 5 |
| C | 3.60 | 86.40 | 10 |
| D | 3.52 | 84.48 | 12 |
| E | 3.48 | 83.52 | 13 |
| F | 3.44 | 82.56 | 14 |
| G | 3.40 | 81.60 | 15 |
| H | 3.36 | 80.64 | 16 |
| I | 3.32 | 79.68 | 17 |
| J | 3.28 | 78.72 | 18 |
| K | 3.24 | 77.76 | 19 |
| L | 3.20 | 76.80 | 20 |
| M | 3.12 | 74.88 | 22 |
| N | 3.00 | 72.00 | 25 |
| O | 2.80 | 67.20 | 30 |
| P | 2.60 | 62.40 | 35 |
| Q | 2.40 | 57.60 | 40 |

INDUSTRIAL APPLICABILITY

As described above, the present invention makes it possible to obtain a porous body with different physical properties in desired regions without bonding materials that have been made porous beforehand to each other. The present invention allows various porous bodies to be produced by merely changing the composition ratios of raw materials and placing frozen bodies with desired shapes through one freeze-drying treatment. Accordingly, the production process of the present invention can be considered as a very useful technique particularly for providing biomaterials in the aforementioned medical fields.

The invention claimed is:

1. A process for producing a porous body with different physical properties in desired regions,
   wherein the process comprises the following (A) to (D):
   (A) providing at least two raw materials having different compositions, each of which contains a polymer and a solvent, wherein at least one of the raw materials is a gelled product that is obtained by the following (A1) to (A3):
      (A1) mixing the polymer and the solvent to prepare a mixture,
      (A2) allowing the mixture to stand to separate the mixture into a liquid phase and a gel phase, and
      (A3) recovering the gel phase as the gelled product,
   (B) freezing the respective raw materials into desired shapes to form frozen bodies of the respective raw materials,
   (C) forming an assembly of the frozen bodies, where at least one of the following (C1) and (C2) is included,
      (C1) forming the assembly of the frozen bodies and then exposing the assembly to a condition under which the frozen bodies begin to melt, and
      (C2) exposing the respective frozen bodies to a condition under which the frozen bodies begin to melt and then forming the assembly of the frozen bodies, and
   (D) freeze-drying the assembly after (C) to form a porous body.

2. The process according to claim 1, wherein the porous body to be formed is a porous body with physical properties varying in its thickness direction, and in (C), the frozen bodies are laminated together to form a laminate of the frozen bodies.

3. The process according to claim 1, wherein the physical properties are at least one selected from the group consisting of an average pore size, porosity, strength, thickness, material permeability, and adhesiveness.

4. The process according to claim 1, wherein in (B), the respective raw materials are frozen under a temperature condition that is equal to or lower than eutectic points thereof.

5. The process according to claim 1, wherein in (B), the respective raw materials are frozen at lower than 0° C.

6. The process according to claim 1, wherein in (C1), the assembly is exposed to a temperature condition that is at least the highest melting point among those of the respective frozen bodies that form the assembly.

7. The process according to claim 1, wherein the assembly in (C1) or the frozen bodies in (C2) are exposed to a temperature condition between 0° C. and 25° C.

8. The process according to claim 6, wherein in (C1) or (C2), a treatment time under the condition is at least 30 seconds.

9. The process according to claim 1, wherein the polymer is a lactide-caprolactone copolymer.

10. The process according to claim 9, wherein in the lactide-caprolactone copolymer, the molar ratio between lactide and caprolactone is in a range of 90:10 to 10:90.

11. The process according to claim 1, wherein the solvent is at least one of a solvent having solubility to the polymer and a mixed solvent containing a solvent having solubility to the polymer and a solvent having insolubility to the polymer.

12. The process according to claim 1, wherein at least one of the raw materials used in (A) is a solution containing the polymer dissolved in the solvent.

13. The process according to claim 12, wherein the amount of the polymer in the solution is 0.1 to 24 wt % based on the total weight of the solution.

14. The process according to claim 1, wherein at least one of the raw materials used in (A) is a solution containing a lactide-caprolactone copolymer dissolved in the solvent,
the solvent contains a solvent having solubility to the copolymer, and
the amount of the solvent having solubility to the copolymer is more than 84.48 wt % based on the total weight of the raw material.

15. The process according to claim 14, wherein the solvent is a mixed solvent containing a solvent having solubility to the copolymer and a solvent having insolubility to the copolymer, and
the amount of the solvent having insolubility is lower than 12 wt % based on the total weight of the raw material.

16. The process according to claim 1, wherein the amount of the polymer in the mixture obtained in (A1) is 0.1 to 24 wt % based on the total weight of the mixture obtained in (A1).

17. The process according to claim 1, wherein the polymer used in (A1) is a lactide-caprolactone copolymer,
the solvent is a mixed solvent containing a solvent having solubility to the copolymer and a solvent having insolubility to the copolymer, and
the amount of the solvent having insolubility is 12 to 40 wt % based on the total weight of the mixture obtained in (A1).

18. The process according to claim 11, wherein the solvent having solubility to the polymer is at least one selected from the group consisting of 1,4-dioxane, dimethyl carbonate, chloroform, and acetone.

19. The process according to claim 11, wherein the solvent having insolubility to the polymer is at least one solvent selected from the group consisting of water, ethanol, tertiary butyl alcohol, and hexane.

* * * * *